United States Patent [19]
Gupta

[11] Patent Number: 5,173,561
[45] Date of Patent: Dec. 22, 1992

[54] HEAT RESISTANT POLYIMIDE-BENZOXAZOLE POLYMERS AND COMPOSITES THEREOF

[75] Inventor: Rakesh K. Gupta, Beavercreek, Ohio

[73] Assignee: Daychem Laboratories, Inc., Fairborn, Ohio

[21] Appl. No.: 558,101

[22] Filed: Jul. 24, 1990

[51] Int. Cl.$^5$ .................... C08G 73/10; C08G 69/28; C08C 73/22; C08J 79/08
[52] U.S. Cl. .................... 528/183; 528/125; 528/126; 528/128; 528/170; 528/172; 528/173; 528/179; 528/184; 528/185; 528/188; 528/191; 528/220; 528/222; 528/229; 528/351; 528/353
[58] Field of Search .............. 528/125, 126, 128, 170, 528/172, 173, 179, 183, 184, 191, 185, 188, 222, 220, 229, 351, 353

[56] References Cited

U.S. PATENT DOCUMENTS

| | | | |
|---|---|---|---|
| 3,745,149 | 7/1973 | Serafini et al. | 528/353 |
| 3,781,249 | 12/1973 | Lubowitz | 528/353 |
| 3,959,350 | 5/1976 | Rogers | 528/353 |
| 4,087,409 | 5/1978 | Preston | 428/474 |
| 4,244,853 | 1/1981 | Serafini et al. | 528/353 |
| 4,305,796 | 12/1981 | Gagliani et al. | 528/353 |
| 4,315,077 | 2/1982 | Gagliani et al. | 528/353 |
| 4,405,770 | 9/1983 | Schoenberg et al. | 528/353 |
| 4,803,147 | 2/1989 | Mueller et al. | 521/164 |
| 4,822,868 | 4/1989 | Mueller et al. | 528/353 |
| 4,845,183 | 7/1989 | Mueller et al. | 528/353 |
| 4,866,155 | 9/1989 | Mueller et al. | 528/353 |
| 4,877,653 | 10/1989 | Vora et al. | 528/353 |
| 4,980,447 | 12/1990 | Khanna | 528/184 |

FOREIGN PATENT DOCUMENTS

| | | |
|---|---|---|
| 0387060 | 9/1990 | European Pat. Off. . |
| 0387061 | 9/1990 | European Pat. Off. . |
| 0387062 | 9/1990 | European Pat. Off. . |
| 0393826 | 10/1990 | European Pat. Off. . |

OTHER PUBLICATIONS

Khanna, Dinesh N., Hoechst Celanese Corporation Publication, pp. 348–349.

Primary Examiner—John Kight, III
Assistant Examiner—P. Hampton-Hightower
Attorney, Agent, or Firm—Frost & Jacobs

[57] ABSTRACT

The present invention relates to a novel class of aromatic diamine monomers, benzoxazole polymers made from said class of monomers, and polymer-matrix composites which may be produced therefrom. The present invention also relates to methods of producing said polymers and said polymer-matrix composites. The polymer-matrix composites have as one advantage high strength and temperature resistance.

27 Claims, No Drawings

HEAT RESISTANT POLYIMIDE-BENZOXAZOLE POLYMERS AND COMPOSITES THEREOF

BACKGROUND OF THE INVENTION

The present invention relates to a novel monomer, polymers made from this monomer and a polymer-matrix composite produced therefrom. The present invention also relates to methods of producing the polymer and the polymer-matrix composite.

The field where the present invention finds one of its beneficial applications is in the manufacture of heat-resistant component materials such as those used in jet aircraft. In this and other applications, it is vital that the materials have both sufficient strength and temperature resistance to perform in environments where the materials are exposed to high stresses and temperatures as well as where such stresses, temperatures and other conditions—such as ambient pressure—may vary widely during the material's performance.

With regard to composite materials, it is important that their components, i.e. the polymer(s) and the matrices from which the composites are made, impart sufficient strength to the composite once formed. Such strength is generally a function of the molecular, microscopic and macroscopic character of the components themselves and that of the polymerization and compositing process which bring about the final product.

As regards the polymer itself, several polymers have been developed to yield high strength. One aspect of polymer design is the use of molecularly rigid chemical moities, adjoined by high bond strength, which in turn impart corresponding rigidity and strength to the finished polymer. An example of polymers of this general type are disclosed, for instance, in U.S. Pat. Nos. 4,097,409 to Preston, 4,845,183 to Mueller, et al. and 4,866,155 to Khanna, et al. However, such polymers have not been advantageously designed to yield the optimal characteristics, both in processing of the composite and in the final composite product itself.

In addition to the strength and heat resistance of the polymer itself, it has been found that it is very important to minimize, or even virtually eliminate, interstitial void spaces in the composite product. Such voids may be caused by the physical processing or by the pressure of volatile substances (usually solvent or volatile by-products of polymerization). Thus it is desirable to create both a combination of polymer and reinforcement, and a polymerization-compositing method which most effectively and efficiently minimizes or eliminates solvent and volatile by-products as the composite is formed.

One of the countervailing considerations, however, is that the polymer must maintain sufficient flow characteristics during processing so that it can easily be processed and brought into intimate contact with the reinforcement. Accordingly, it is required that, although solvent be finally removed, that the polymer be able to maintain appropriate flow characteristics throughout the polymerization compositing process.

With regard to the minimization of volatile by-products, it is desirable to create polymer systems which have the advantages of (1) producing relatively small amounts of volatile by-products and (2) being amenable to processing which removes most of the volatiles before they can affect the integrity of the final composite product (i.e. before the final curing step).

SUMMARY OF THE INVENTION

In order to solve the problems associated with prior art methods and materials, and to provide the above advantages, the present invention provides a novel monomer and method of its production, a polymer from said monomer, a method of processing said polymer, and a method of preparing a polymer-matrix composite therefrom.

The novel compounds of the present invention have the following structural formula:

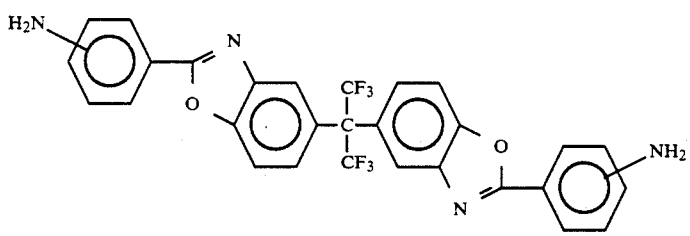

wherein the amino groups may be at the meta or para positions from the benzoxazole ring. The para isomer is referred to herein as $DCM_1$ while the meta isomer is referred to herein as $DCM_2$.

These monomers may be prepared by any appropriate synthetic method. However, the present invention involves a specific method of making these monomers. This method involves the following general steps.

The first step is to nitrate the following compound:

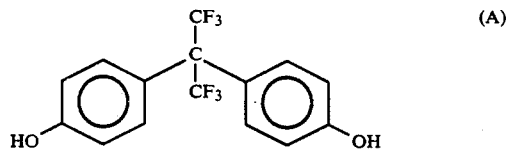

such as Biophenol-AF available from Hoechest-Celanese, so as to form:

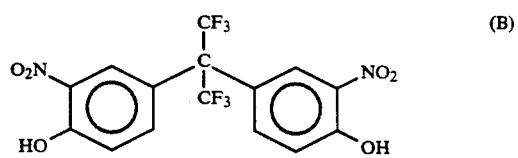

This may be done with any appropriate nitrating agent such as nitric acid.

Compound B above is then reduced to form:

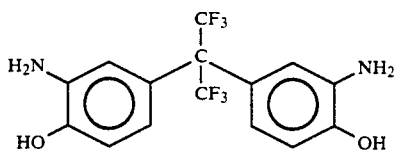
(C)

by use of any appropriate reducing agent known in the art such as palladium on carbon and hydrogen gas.

Compound C is in turn reacted with two equivalents of either meta- or para- amino benzoic acid (or a mixture thereof) so as to form benzoxazole moieties from the benzoic acid groups of the benzoic acid molecules and the hydroxyl and amino groups of Compound C so as to produce:

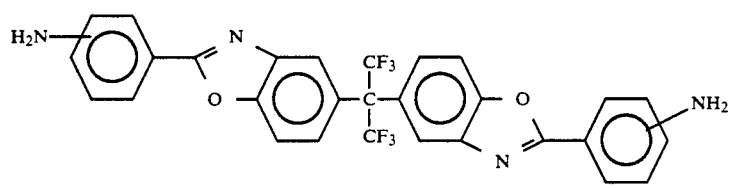
(D)

or a mixture thereof, respectively, wherein the position of the amino groups (meta or para) corresponds to that of the amino group in the meta- or para- benzoic acid, respectively.

The benzoxazole monomer (Compound D above) may in turn be used to produce high strength, heat resistant polymers by reaction with at least one aromatic bicyclic dianhydride, such as:

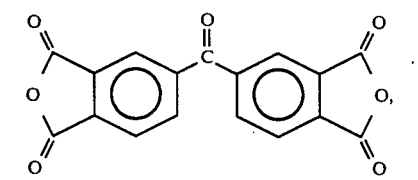
(E)

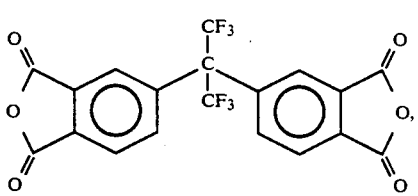
(F)

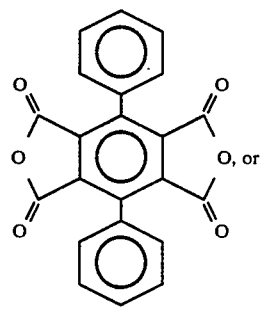
O, or

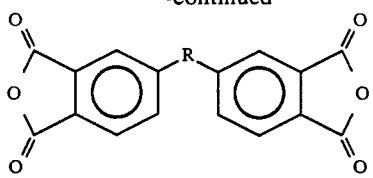
-continued wherein R is selected from intra molecular groups having from 1 to 10 carbon atoms. The dianhydrides which may be used in accordance with the present invention may also include anhydride-terminated oligomers. Equivalent dianhydrides which give appropriate characteristics may be used. These characteristics include solubility in organic solvent, the ability to form stable and rigid polymeric linkages, and preferably large size to minimize the by-products produced in the polymerization reaction, and low volatility to reduce toxicity. Such dianhydrides generally include those having the appropriate geometrical characteristics and/or functionalities (such aromatic and/or cyclic moieties or other groups such as the hexafluoroisopropyl moiety in (F) above) which impart molecular rigidity to the polymer product. Such polymerization has been found to be carried out most advantageously by first reacting the dianhydride with a low-molecular weight solvent capable of reacting with the dianhydride moiety. Examples of such a solvent are methanol and ethanol. This reaction yields the diester-diacid analog, as shown below when methanol is reacted with Compound E:

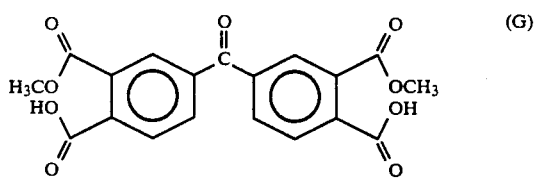
(G)

The aromatic diester-diacid compound may then be reacted with either of the compounds represented in structure D (or a mixture thereof) to yield an amide-linked/acid polymer. This is formed by the ester moieties of the diester each condensing with the respective amine groups of the above diamine compound(s) shown in structure D. This step is usually carried out at a temperature in the range of from about 250° to about 275° F. In the production of such polymers, the removal of water and solvent by-product is often desirable. In such cases, the formation of the amide-linked/acid polymer can be carried out under vacuum, for instance at about 0.3" of mercury.

Such a reaction involving for example the diester-diacid Compound G reacting with the para isomer of structure D yields a polymer having the following repeating structural unit:

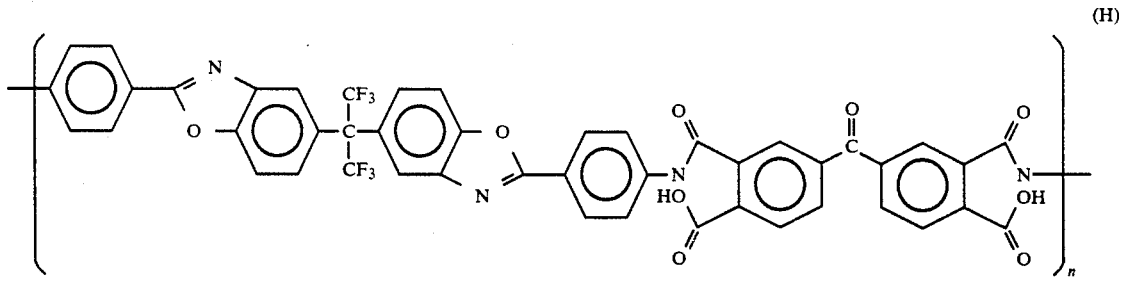

(H)

wherein n is a real number.

The resultant amide-linked/acid polymer may then be further cured by causing the amide-linkage and the neighboring acid moiety to cyclize, so as to form a polymer having repeating subunits exemplified by the following structure using the precursor structure (H), yielding:

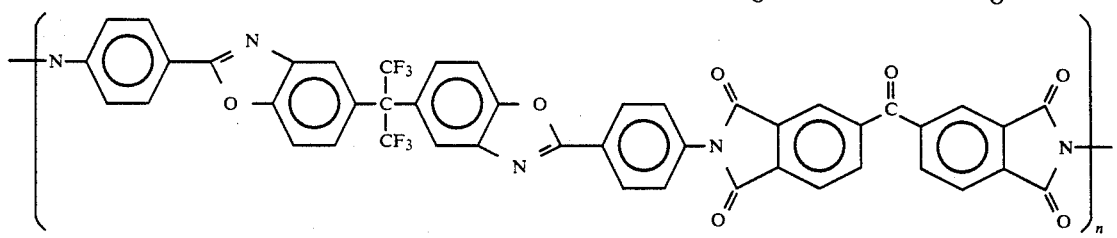

(I)

wherein n is a real number.

The cyclization of the polymer linkages as well as further polymerization of oligomers so formed may be carried out under vacuum to remove excess water and solvent. The cyclization is preferably initially carried out at a temperature of about 475° F. for about 1 hour. Further polymerization can be carried out at higher temperatures such as 600° F. and may involve longer reaction times such as about three hours.

A variation of the present invention involves the analogous use of at least one organic diacid such as terephthalic acid (para-carboxybenzoic acid) in place of the dianhydride(s) used above. As with the dianhydrides which may be used in accordance with the present invention, it is preferred that the organic diacids be those whose geometric and functional characteristics which impact appropriate rigidity to the polymer.

The stoichiometry of the oligomer-forming reaction may be altered to control the size of the oligomer formed. Preferably, the stoichiometry is maintained with the range of 5:4 to 4:5 with respect to diamine/dianhydride (or diacid), and is most preferably 1:1.

A further variation of either the method reacting (1) the cyclic dianhydride(s) or (2) organic diacid(s) with the diamine is to include in the polymer-forming mixture at least one chemical compound which will form cross-linking end cap oligomers with either the resulting (1) amide-linked/acid oligomer or (2) amide-linked oligomer, respectively. These compounds may also be reacted with the diamine alone. Such compounds may include any chemical compound(s) with the appropriate organic functionality(ies) required to form the cross-linking end cap oligomers, such as meta-amino phenyl acetylenes for dianhydride-terminated oligomers. Other compounds include styrene, benzocyclobutene and biphenyl. Another example is the formation of bismaleimides by the following:

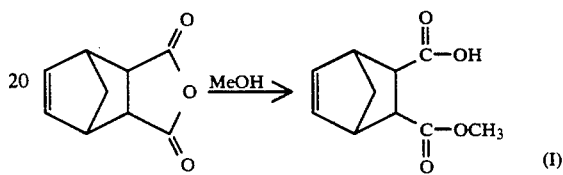

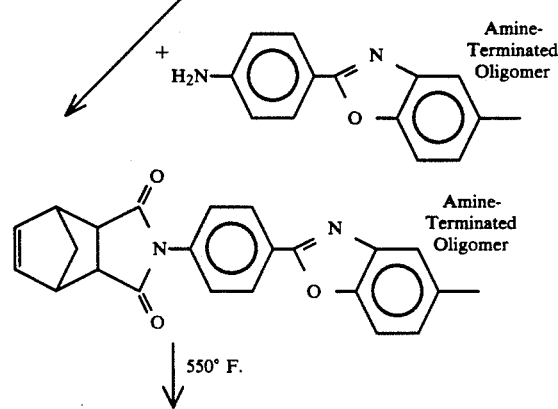

-continued

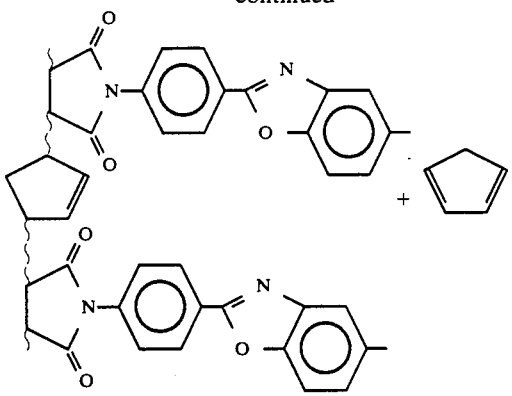

An analogous compound which may be employed in similar fashion for amine-terminated oligomers as above is maleic anhydride.

The production of a polymer-matrix composite is carried out using the same fundamental polymer-forming steps described above while bringing the reaction mixture into contact with a matrix prior to finally curing the polymer so the polymer is ultimately cured in situ in intimate contact with the chosen matrix.

Any appropriate matrix may be used in accordance with the desired application of the composite product. The matrix may be in any physical form such as in the form of powders, particles or fibers, of various lengths, shapes and sizes again depending upon application ingredients. For instance, the fiber may be in the form of longer fibers which are wound into a given shape such as upon a mandrel after being placed in intimate contact with the polymer reaction mixture. This may be done using a mandrel apparatus. The preferred matrix for making any number of high strength, heat resistant articles is carbon fiber. Other matrices include fiberglass, KEVLAR ®, quartz, nylon, etc.

DETAILED DESCRIPTION OF THE PREFERRED EMBODIMENT

In the preferred embodiment of the present invention, Compound E is admixed with an excess of methanol to bring about the diester-diacid Compound G. The amide-linked/acid oligomer (See structure H) is formed by addition of $DCM_1$ or $DCM_2$, or mixture thereof, in desired stoichiometry (See structure D). The bulk of the methanol, beyond that necessary to maintain the mixture as a liquid, is removed either by evaporation at room temperature, by vacuum, or by heating below 80° C.

This reaction is carried out at a temperature in the range of from about 250° to about 275° F. A vacuum of at least about 0.3" of mercury is applied to remove excess solvent and water reaction. This polymerization is carried out only to the point that the homogeneity of solution compatability of the mixture is maintained so as to provide easiest application to the matrix and allow volatiles to escape most efficiently as compositing is initiated. The reaction time is generally about ½ hour for this step.

At this point, it is preferred that the reaction mixture be brought into intimate contact with the chosen reinforcement—in this case, carbon fiber prepared to be wound onto a mandrel.

In the next step, the amide-linked/acid oligomer is cyclized so as to form the imide-linked polymer shown in structure I. This step is also carried out under vacuum, preferably more strenuous vacuum of at least 28 inches of mercury, to remove the remaining volatiles such as solvent and water of reaction The cyclization step is preferably carried out for about one hour.

The composite is placed under high pressure, e.g. about 200 p.s.i., so as to best produce the polymer composite.

Finally, the polymer is completely cured by completing the cyclization reaction throughout the polymer and elongating the polymer through further polymerization. This final cure step is also carried out with the composite maintained under 200 p.s.i. pressure while under the more strenuous vacuum of at least 28 inches of mercury. The temperature is preferably elevated during the final cure (to about 600° F.) and the reaction time is generally about three hours.

The following examples accurately represent exemplary embodiments of the invention.

EXAMPLE I

Production of DCM-1

2,2 Bis (3-amino-4-hydroxphenyl) hexafluoropropane (500 gm, 1.36 mols) was dissolved in PPA (4 kg) at 70° C. and aminobenzoic acid (375 gm, 2.72 moles) was added slowly over a period of 1 hour. The resulting solution was heated at 115° C. for 1 hour, the temperature was then raised to 185° C. and stirred for 12 hours at this temperature. It was poured over crushed ice, the precipitated material filtered out and washed with 10% $NH_4OH$ solution. This material was then suspended in water, filtered, dried under vacuum to constant weight and crystallized from methanol-water to afford the pure DCM-1 (650 gm, 84% yield), m.p. 254°–255° C.

EXAMPLE II

Polymer Production Using DCM-1 and DCM-2 (DCL 3.2)

A 5L flask is equipped with a reflux condenser, stirrer and thermometer. 3½ L of methanol is added to the flask and heated to reflux 215.2 g of BTDA is slowly added. The BTDA/Methanol solution is stirred for 1 hour after the BTDA goes into solution. 189.8 g of DCM-1 is added slowly and the solution stirred until clear. 189.8 g of DCM-2 is added to the solution slowly and the solution stirred until clear. The mixture is cooled under stirring and a vacuum applied to remove the excess methanol. When a total weight of 915.1 g of the resin is measured, the percent solids is 65%.

EXAMPLE III

Polymer Production Using DCM-1 Only (DCL 1.2)

The same procedure is followed but 379.6 g of DCM-1 only is added slowly to the methanol/BTDA solution. A large excess of methanol is required to force the DCM-1 into solution. No DCM-2 is added. All other reactants are in the same amounts.

Results

The following results were obtained in comparing polymer resins DCL 1.2 and DCL 3.2 to resin representative of the prior art (PMR-15).

Table I presents Thermo Oxidative Stability (TOS) weight loss results for the two DCL resins and PRM-15 laminates on glass cloth. The flat laminate specimens were tested at 650° F. and 4 atmospheres pressure for 100 hours.

TABLE I

DCL/GLASS CLOTH AND PMR-15/GLASS CLOTH THERMO OXIDATIVE STABILITY DTA

| | EB-8 | EB-9 | EB-10 | EB-10 PC* | EB-11 |
|---|---|---|---|---|---|
| Resin | DCL 1.2 | PMR-15 | DCL 3.2 | DCL 3.2 | DCL 1.2 |
| Resin Content | 52 | 30 | 28 | 28 | 49 |
| Void Content (% volume) | 7.3 | 0 | 0.8 | 0.8 | 12.9 |
| Resin Weight Loss (%)** | 6.12 | 37.2 | 5.54 | 5.62 | 8.68 |

*Postcured at 700° F. for 3 hours.
**Weight loss as a percentage of original resin weight.
NOTES:
1. Test conditions:
A. 650° F.
B. 100 hour
C. 4 atmospheres pressure.
2. Data averages of two specimens each.
3. Neat resin weight loss data at this condition:
A. Avimid N 1.60 percent
B. DCL-1 3.74 percent
C. PMR-II 4.37 percent
D. PMR-15 7.07 percent Table II presents flexural property data on these samples of DCL 1.2 resin produced on glass panels and cured for one-half hour at 250° F., one hour at 475° F. and three hours at 600° F. Full vacuum was applied.

TABLE II

FLEXURAL PROPERTIES OF DCL 1.2
ASTM D790 (3 POINT LOADING)

| I.D. No. | AREA sq in | ULT LBS | X-HEAD (IN) | ULT STRAIN | FIBER STRESS (KSI) | MODULUS (MTI) |
|---|---|---|---|---|---|---|
| 1 | .0288 | 97 | .07525 | .0253 | 90.1 | 4.23 |
| 2 | .0305 | 116 | .077 | .0268 | 97.9 | 4.34 |
| 3 | .0296 | 96 | .07425 | .0258 | 83.5 | 3.77 |
| MEAN | | 103 | .076 | .026 | 90.5 | 4.113 |
| STD | | 11.269 | .001 | .001 | 7.209 | .302 |
| CO VAR % | | 10.941 | 1.844 | 2.942 | 7.965 | 7.351 |

Tests were conducted on samples prepared in accordance with the following summary:

DCL RESIN EVALUATION TASK SUMMARY

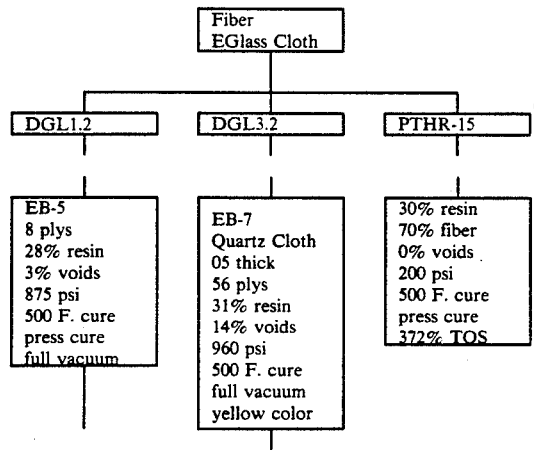

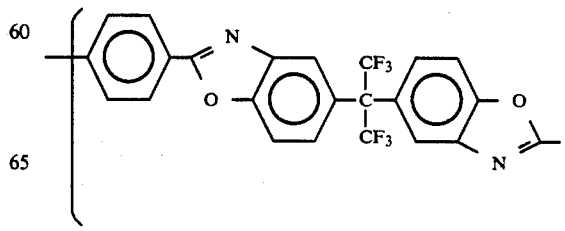

*commercial polyimide for control purposes.

Depending upon the compositing method, matrix type and form and other parameters whose modifications will be within the capability of one of ordinary skill, composites of various types and shapes can be prepared in accordance with the present invention. Modification may be made to the parameters of the above-disclosed invention without departing from its spirit.

What is claimed:

1. A polymer having the following recurring structural unit:

-continued

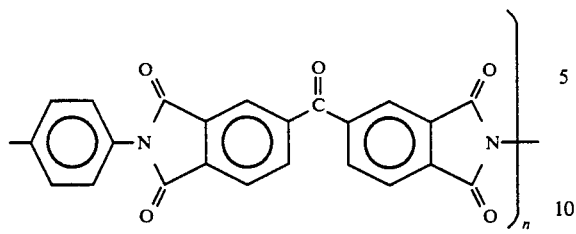

wherein n is a real number.

2. A process for preparing a heat resistant polymer-matrix composite comprising:
   (a) reacting at least one aromatic bicyclic dianhydride on anhydride-terminated oligomer having the ability to form stable and rigid polymeric linkages with at least one solvent having a boiling point below about 475° F. capable of reacting with said dianhydride or anhydride-terminated oligomer so as to form an aromatic diester-diacid compound;
   (b) reacting said diester-diacid compound with at least one diamine compound selected from the group consisting of:

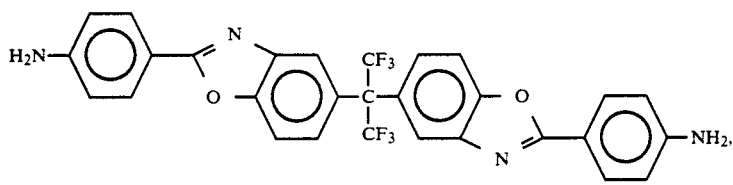

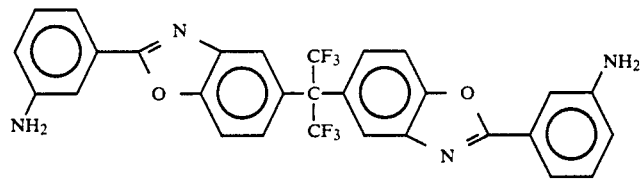

and mixtures thereof for sufficient time and at sufficient temperature to produce an amide-linked/acid oligomer of said at least one diester-diacid compound and said at least one diamine compound;
   (c) placing said amide-linked/acid oligomer in contact with at least one matrix; and
   (d) cyclizing said amide-linked/acid oligomer so as to produce an imide-linked polymer; and further polymerizing said imide-linked polymer at sufficient temperature, under sufficient pressure and for sufficient time so as to form a polymer-matrix composite.

3. A process according to claim 2 wherein said at least one diester-diacid compound and said at least one diamine compound are present in a ratio of about 1:1.

4. A process according to claim 2 wherein said solvent is methanol.

5. A process according to claim 2 wherein said aromatic bicyclic dianhydride is selected from the group consisting of the compounds having the formulae:

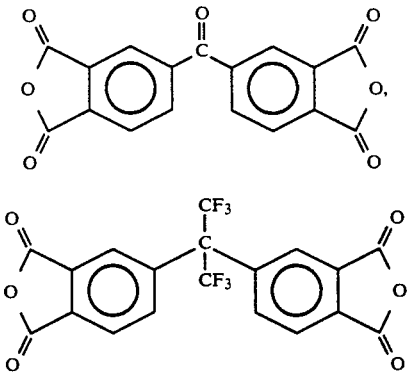

and mixtures thereof.

6. A process according to claim 2 additionally comprising the step of removing an amount of said solvent beyond that necessary to maintain said diester-diacid compound in a liquid form before reaching step (c).

7. A process according to claim 6 additionally comprising the step of replacing said portion of solvent removed from said reaction prior to step (c) with ethanol before proceeding to step (c).

8. A process according to claim 2 wherein (a) is carried out at a temperature below 80° C.

9. A process according to claim 2 wherein step (b) is carried out at a temperature of from about 250 to about 275° F. under a vacuum of about 0.3 inches of mercury for about ½ hour.

10. A process according to claim 2 wherein step (d) is carried out with said amide-linked/acid oligomer under a pressure of about 200 p.s.i., at a temperature of about 475° F. and under a vacuum of about 0.3 inches of mercury for about 1 hour.

11. A process according to claim 2 wherein said further polymerization is carried out with said amide-linked/acid oligomer-matrix composition under a pressure of about 200 p.s.i., at a temperature of about 600° F. and under a vacuum of about 0.3 inches of mercury for about 3 hours.

12. A process according to claim 2 wherein said matrix is a carbon fiber.

13. A process according to claim 2 wherein said matrix may be in a form selected from the group consisting of powders, particles and fibers.

14. A polymer-matrix composite produced according to the process of claim 2.

15. A process according to claim 2 additionally comprising reacting said amide-linked/acid oligomer with at least one chemical compound containing a functionality chosen from the group consisting of acetylene, styrene, benzocyclobutene, biphenyl, norbornene, maleic, and mixtures thereof, so as to form a cross-linked end cap oligomer on said amide-linked/acid oligomer.

16. A process according to claim 2 additionally comprising reacting said at least one diamine with at least one chemical compound containing a functionality chosen from the group consisting of acetylene, styrene, benzocyclobutene, biphenyl, norbornene, maleic, and mixtures thereof, so as to form a cross-linked end cap oligomer on said amide-linked/acid oligomer.

17. A process of preparing a polymer comprising:
(a) reacting at least one aromatic diacid compound with at least one diamine compound selected from the group consisting of:

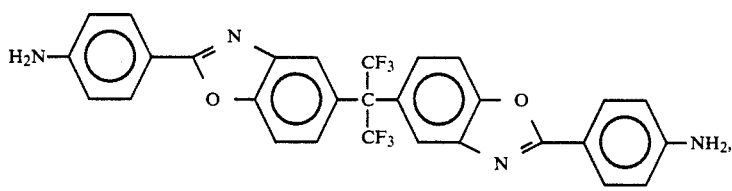

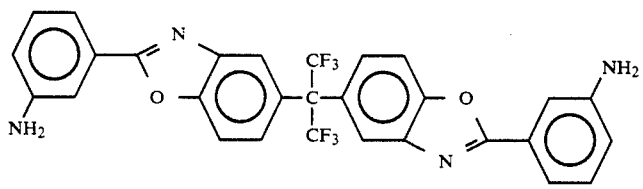

and mixtures thereof, for sufficient time and at sufficient temperature to produce an amide-linked polymer at said at least one aromatic diacid compound and said at least one diamine compound.

18. A process for preparing a heat resistant polymer-matrix composite comprising:
(a) reacting at least one aromatic diacid compound with at least one diamine compound selected from the group consisting of:

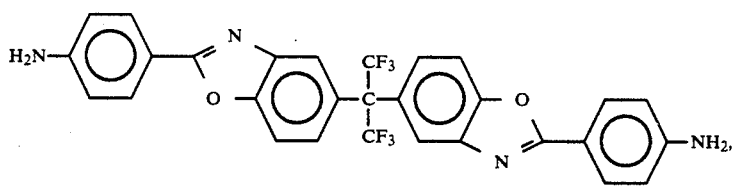

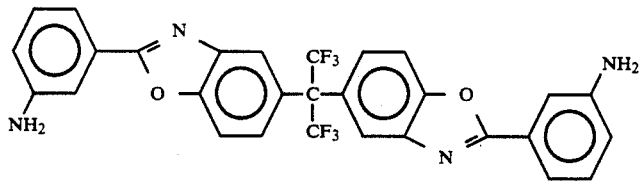

and mixtures thereof in a solvent for sufficient time and at sufficient temperature to produce an amide-linked oligomer of said at least one aromatic diacid compound and said at least one diamine compound;

(b) placing said amide-linked oligomer in contact with at least one matrix; and
(c) further polymerizing said amide-linked oligomer at sufficient temperature, under sufficient pressure and for sufficient time so as to form a polymer-matrix composite.

19. A process according to claim 18 wherein said at least one organic diacid compound and said at least one diamine compound are present in a ratio of about 1:1.

20. A process according to claim 18 wherein said solvent is methanol.

21. A process according to claim 18 wherein said organic diacid compound is para-carboxybenzoic acid.

22. A process according to claim 18 additionally comprising the step of removing an amount of said solvent beyond that necessary to maintain said amide-linked oligomer in a liquid form before reaching step (c).

23. A process according to claim 22 additionally comprising the step of replacing said portion of said solvent removed from said reaction prior to step (c) with ethanol before proceeding to step (c).

24. A process according to claim 18 additionally comprising reacting said amide-linked oligomer with at least one chemical compound containing a functionality chosen from the group consisting of acetylene, styrene, benzocyclobutene, biphenyl, norbornene, maleic, and mixtures thereof, so as to form a cross-linking end cap oligomer on said amide-linked/acid oligomer.

25. A process according to claim 18 additionally comprising reacting said at least one diamine with at least one chemical compound containing a functionality chosen from the group consisting of acetylene, styrene, benzocyclobutene, biphenyl, norbornene, maleic, and mixtures thereof, so as to form a cross-linking end cap oligomer on said amide-linked/acid oligomer.

26. A process for preparing a heat resistant polymer-matrix composite comprising reacting:
(a) at least one organic diacid with at least one diamine compound with at least one diamine compound selected from the group consisting of:

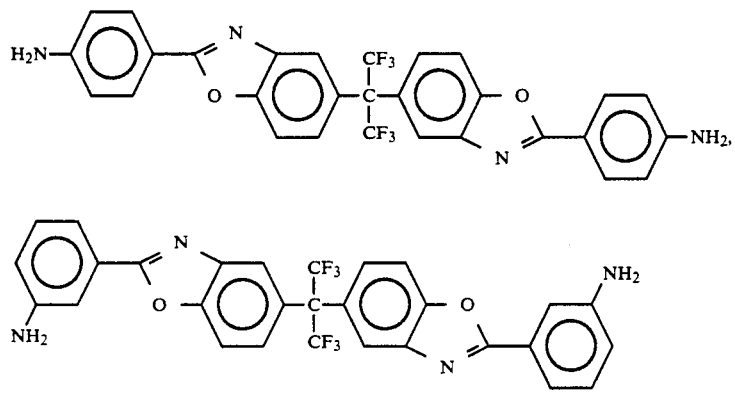

and mixtures thereof for sufficient time and at sufficient temperature to produce an amide-linked oligomer of said at least one organic diacid compound and said at least one diamine compound;
(c) placing said amide-linked oligomer in contact with at least one matrix; and
(d) further polymerizing said amide-linked oligomer at sufficient temperature, under sufficient pressure and for sufficient time so as to form a polymer-matrix composite.

27. A process according to claim 26 wherein said at least one organic diacid compound and said at least one diamine compound are present in a ratio of about 1:1.

* * * * *

UNITED STATES PATENT AND TRADEMARK OFFICE
CERTIFICATE OF CORRECTION

PATENT NO. : 5,173,561
DATED : December 22, 1992
INVENTOR(S) : Rakesh K. Gupta

It is certified that error appears in the above—identified patent and that said Letters Patent is hereby corrected as shown below:

Column 11, claim 2, line 17, "on" should be deleted and replaced with --or--.

Column 15, claim 26, lines 7-8, "at least one diamine compound with" should be deleted.

Signed and Sealed this

Ninth Day of November, 1993

Attest:

BRUCE LEHMAN

Attesting Officer    Commissioner of Patents and Trademarks